(12) United States Patent
Berndsen

(10) Patent No.: US 8,346,334 B2
(45) Date of Patent: Jan. 1, 2013

(54) MEDICAL SENSOR

(75) Inventor: Lars Berndsen, Gaertringen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 1374 days.

(21) Appl. No.: 11/996,605

(22) PCT Filed: Jul. 27, 2006

(86) PCT No.: PCT/IB2006/052579
§ 371 (c)(1),
(2), (4) Date: Jan. 24, 2008

(87) PCT Pub. No.: WO2007/013042
PCT Pub. Date: Feb. 1, 2007

(65) Prior Publication Data
US 2008/0200786 A1 Aug. 21, 2008

Related U.S. Application Data

(60) Provisional application No. 60/595,710, filed on Jul. 29, 2005.

(51) Int. Cl.
*A61B 5/1455* (2006.01)
(52) U.S. Cl. .......................... 600/344; 600/322; 600/323
(58) Field of Classification Search .................. 600/310, 600/322, 323, 344, 473, 476; 356/41
See application file for complete search history.

(56) References Cited

U.S. PATENT DOCUMENTS

| | | | | | |
|---|---|---|---|---|---|
| 4,825,879 | A | * | 5/1989 | Tan et al. | 600/344 |
| 4,830,014 | A | * | 5/1989 | Goodman et al. | 600/310 |
| 5,425,360 | A | | 6/1995 | Nelson | |
| 5,782,757 | A | * | 7/1998 | Diab et al. | 600/323 |
| 5,891,026 | A | | 4/1999 | Wang et al. | |
| 5,999,834 | A | * | 12/1999 | Wang et al. | 600/344 |
| 6,466,809 | B1 | * | 10/2002 | Riley | 600/344 |
| 6,622,034 | B1 | | 9/2003 | Gorski et al. | |
| 2002/0173708 | A1 | | 11/2002 | DeLonzor et al. | |
| 2003/0181799 | A1 | | 9/2003 | Lindekugel et al. | |
| 2006/0149149 | A1 | * | 7/2006 | Schmid | 600/473 |

FOREIGN PATENT DOCUMENTS

| | | |
|---|---|---|
| EP | 0127947 A2 | 12/1984 |
| EP | 1095612 A1 | 5/2001 |
| WO | 0103574 A1 | 1/2001 |
| WO | 2004069047 A1 | 8/2004 |
| WO | 2006111875 A1 | 10/2006 |

* cited by examiner

*Primary Examiner* — Eric Winakur
*Assistant Examiner* — Chu Chuan (JJ) Liu

(57) ABSTRACT

A medical sensor that allows wrapping about an applied part while maintaining the alignment of the detector and emitter is provided. The medical sensor includes a carrier band that can accommodate variably sized applied parts without misaligning the detector and emitter. The medical sensor can provide space between the skin of the applied part and the emitter and detector. The medical sensor carrier band can be designed with a flexible region and thicker mounting sections that act as spring-loaded mounts when the carrier band is secured in a wrapped position.

15 Claims, 6 Drawing Sheets

MEDICAL SENSOR

CROSS REFERENCE TO RELATED APPLICATIONS

This application claims the benefit of U.S. Provisional Application Ser. No. 60/595,710 filed Jul. 29, 2005, which is incorporated herein by reference.

The present invention relates to medical sensors applied to a patient body for monitoring or making measurements of body conditions, metabolism, or other functions indicative of the patient's health. One particular type of medical sensor is a pulse oximetry sensor that can be used to monitor the level of oxygenation in a patient's blood.

Electronic medical sensors have long been used to monitor pulse and oxygen saturation levels in patients. Monitoring a patient's pulse and oxygen saturation level in the patient's blood can be indicative of the patient's overall wellbeing and can provide signs indicating that the patient's health is at risk. Typically, a transmitter or emitter is secured to one side of the patient's body part, such as a finger or an earlobe, and a receiver or detector is secured on the opposite side of the patient's body part, directly opposite the transmitter. The transmitter emits red and infrared light and the receiver detects these light waves. Based on the relative strength of the signals received, the level of oxygenation of the patient's blood can be determined. The oxygenation level can be monitored and displayed as a saturation percentage known as "SpO2". This parameter provides valuable information to the clinician regarding the functioning of the patient's lungs, heart, and blood circulation.

Medical sensors, such as those described above, are attached to a patient in a quick and removable manner. The medical sensor should be capable of being readily attached to a body part, comfortable when attached to a patient, easily removable, and relatively inexpensive to manufacture. Some medical sensors are used for long-term monitoring, while other medical sensors are merely used for spot-checking. Some medical sensors are reusable for multiple patients, while other medical sensors are designed for single-patient use.

Regardless of the contemplated use of the medical sensor, the medical sensor should provide a means for quickly and easily attachment to and removal from a patient's body part. Generally there are three types of medical sensor attachment means. First, there are hinged mechanisms wherein the transmitter is mounted on one leg of the mechanism and the receiver is mounted on another leg of the mechanism. A spring-loaded pivot assures alignment while accommodating varying thickness of the applied part. Second, a sleeve-mounted mechanism provides for a transmitter and a receiver mounted on opposite sides of a soft sleeve that slides over the applied part. Third, a wrap-mounted mechanism provides a transmitter and a receiver mounted on a strip of flexible material that is wrapped around the applied part. The wrap-mounted mechanism typically includes an adhesive, hook-and-loop fastener, or other means for maintaining the wrap in position on the applied part.

Generally, wrap-mounted medical sensors are preferred for single-patient or disposable uses since they are least costly. However, one major problem with wrap-mounted medical sensors is that the detector and emitter often can be misaligned from one another, depending on the size of the applied part. In order to adjust for variability in the size of the applied part, the effective length of the carrier band is adjusted. As the length of the carrier band is adjusted, the transmitter and receiver shift, thereby losing their alignment.

FIG. 1 illustrates this problem. In the first scenario, on the left, a thinner finger is the applied part and the emitter and detector are aligned. As shown in the second scenario, on the right, a larger finger is the applied part. The carrier band "stretches" to accommodate the larger applied part. However, since all of the compensation that the thin, rigid band can make is on a single side, the emitter and detector do not remain aligned. Although FIG. 1 may exaggerate the misalignment of emitter and detector that results from applied parts of variable size, even slight misalignments can affect the effectiveness and operation of the medical sensor.

Another problem with wrap-mounted medical sensors is that they must be designed with both functionality and comfort in mind. This means that the design of wrap-mounted sensors is very sensitive to the thickness of the carrier band. To be functional, the carrier must be thick enough to retain the electronic components reliably, yet remain sufficiently flexible to conform to the patient's anatomical shape. To be comfortable, the carrier band must expand or compress to fit the variable size of the applied parts. In addition, the amount of thermal energy that is applied to the skin of the applied part must also be controlled.

As such, it is desirable to provide a wrap-mounted medical sensor that solves one or more of these problems.

The present invention is directed to an improved medical sensor. In some embodiments, the improved medical sensor is comprised of a flexible foam that accommodates variably sized applied parts, while maintaining alignment of the detector and emitter. In some embodiments, the medical sensor includes windows that provide space between the patient's skin and the emitter and/or the detector. In some embodiments, the medical sensor includes a carrier band with a relatively thin portion that provides flexibility and one or more thicker portions that act as spring-loaded mounts when the carrier band is secured in a wrapped position.

In the accompanying drawings, which are incorporated in and constitute a part of this specification, embodiments of the invention are illustrated, which, together with a general description of the invention given above, and the detailed description given below serve to illustrate the principles of this invention. One skilled in the art should realize that these illustrative embodiments are not meant to limit the invention, but merely provide examples incorporating the principles of the invention.

The medical sensor disclosed herein provides a wrap-mounted mechanism that maintains alignment of the emitter and the detector with variably sized applied parts. The medical sensor further allows for comfortable application to variably sized applied parts.

Figure 1:
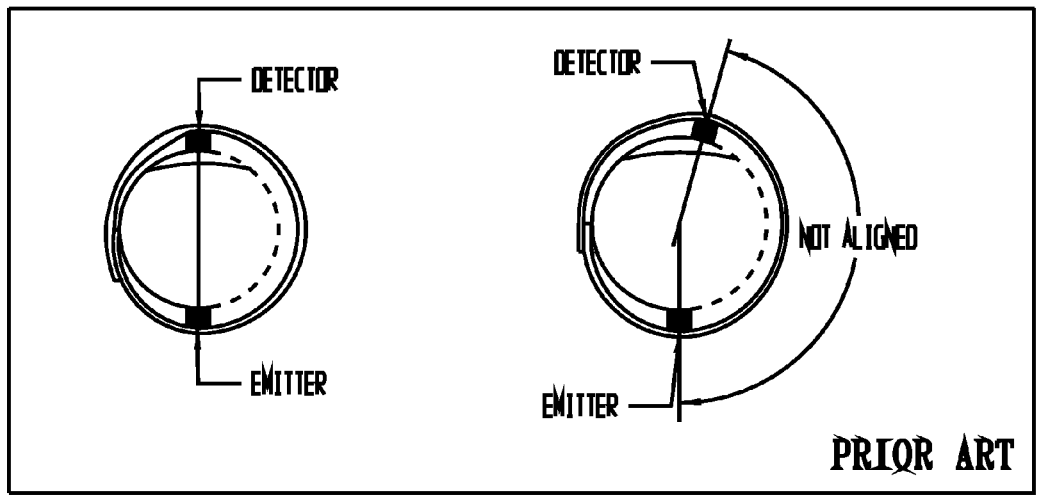
FIG. 1 illustrates a prior art wrap-mounted medical sensor with variably sized applied parts.
Figure 2:
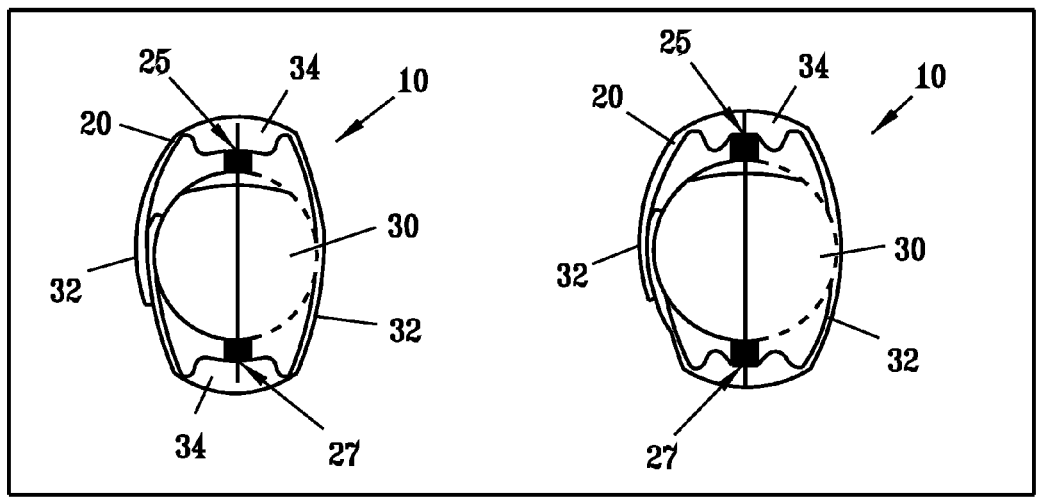
FIG. 2 illustrates an embodiment of the medical sensor of the present invention secured to variably sized applied parts.

The medical sensor 10, as shown in FIG. 2, includes a carrier band 20, detector 25 and emitter 27. The medical sensor 10 can adjust to variably sized applied parts 30 and maintain the alignment of the detector 25 and emitter 27. The term carrier band is used to generally describe a three dimensional component or that wraps around the applied part and is not meant to be limited to any particular shape, size or dimension.

The carrier band 20 can be any adjustable foam material, and in some embodiments is a thermo-formed polyethylene foam. The contour of the carrier band 20 is designed to accommodate variably sized applied parts 30, while maintaining alignment of the detector 25 and emitter 27. The ability of the carrier band 20 to accommodate variably sized applied parts 30 is illustrated in FIG. 2. The carrier band 20 is also designed to allow for easy application and removal from an applied part 30. As shown in FIG. 2, when the carrier band 20 is applied to an applied part 30, the carrier band 20 includes thin sidewalls 32 and thicker end portions 34. The thin sidewalls 32 allow the carrier band 20 to flex as required to fit the contour of the applied part 30. The thicker end portions 34 of the carrier band 20 provide mounting areas for the detector 25 and emitter 27. In addition, the thickness of the end portions 34 can effectively act as a spring to allow the carrier band 20 to be easily secured to an applied part 30 with the detector 25 and emitter 27 aligned. The thin sidewalls 32 and the thick end portions 34 permit radial variability in the radial size of the applied part 30 without affecting the alignment of the detector 25 and emitter 27. This type of design further provides a comfortable fit for the applied part 30, since the carrier band 20 can flex to accommodate the variably sized applied part 30.

Figure 3:
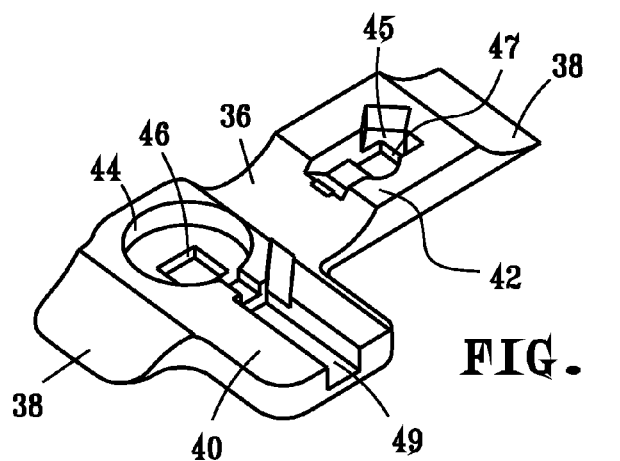
FIG. 3 illustrates an embodiment of a carrier band for a medical sensor.

FIG. 3 illustrates a more detailed embodiment of the medical sensor 10. In this embodiment, the carrier band 20 includes a thin groove 36 for flexing, thin ends 38 for securing the carrier band, a thick area 40 for mounting a receiver or detector 25, and a thick area 42 for mounting a transmitter or emitter 27. The thin sections of the carrier band 20, thin ends 38, can flex to facilitate wrapping around the applied part 30.

As shown in FIG. 3, the carrier band 20 includes a recess 44 for mounting the detector 25 and a recess 45 for mounting the emitter 27. Each of these recesses 44, 45 include a "window" 46, 47 that keeps the warm electronic components, namely the detector 25 and emitter 27, a distance from the patient's skin. In some embodiments, each of the windows 46, 47 create a separation of approximately 1 mm. The windows 46, 47 can create more or less than a 1 mm separation distance from the patient's skin. Additional recessed areas 49 can be formed in the carrier band 20 to accommodate other components or wires, such as those shown in FIG. 4.

In some embodiments, the windows 46, 47 comprise cut out sections in the compressed foam sections of the carrier band 20. The cut out sections are then covered on either side by a layer, such as, for example, an adhesive layer, that creates an air gap between the two layers. Examples of these layers are provided for in the illustrated embodiment shown in FIGS. 4-8, which is discussed in further detail below. The air gap provides insulation between the skin of the applied part and the electrical components, such as the emitter. Windows can exist for each component or either one of the components. Since the foam surrounding the window has been compressed, the air gap between the layers remains a fairly constant predetermined distance when the medical sensor is applied to the applied part. In some embodiments, the windows are not cut out regions, but instead are thin foam regions. In these embodiments, the thickness of the foam can be used to defuse the light as it travels therethrough to the patient's skin.

In order to form the illustrative carrier band 20 shown in FIG. 3, a sheet of polyethylene foam of approximately 3 mm thickness is captured within a metal form. The metal form can be heated and cooled as desired. Parts of the metal form cut the periphery and the internal openings 46, 47 in the carrier band 20. Other portions of the metal form simultaneously compress the foam polyethylene to form areas of thinner thickness. For example, the recesses 44, 45, 49 can be compressed to approximately 1 mm thick. Heat is then applied to the work-piece to soften the foam. The metal form is then cooled while the pressure applied to the foam is maintained. When the work-piece cools sufficiently, it is removed from the metal form and retains the thickness imposed by the tool. Subsequently, electrical components 25, 27 are inserted into the recesses 44, 45, 49 and secured with adhesive or other means. Closure means are applied, typically to the thin ends 38. The closure means can be any type of closure mechanism, such as, for example, buckles, adhesive discs, hook-and-loop fasteners, snapping mechanisms, etc.

In some embodiments, the carrier band 20 is formed from separate foam pieces, which are secured together to form the desired design of the carrier band. In such embodiments, the foam could be cut to size with a die or a laser and then laminated into an assembly. A die or laser could also be used to form the one-piece carrier band described above.

Figure 4:
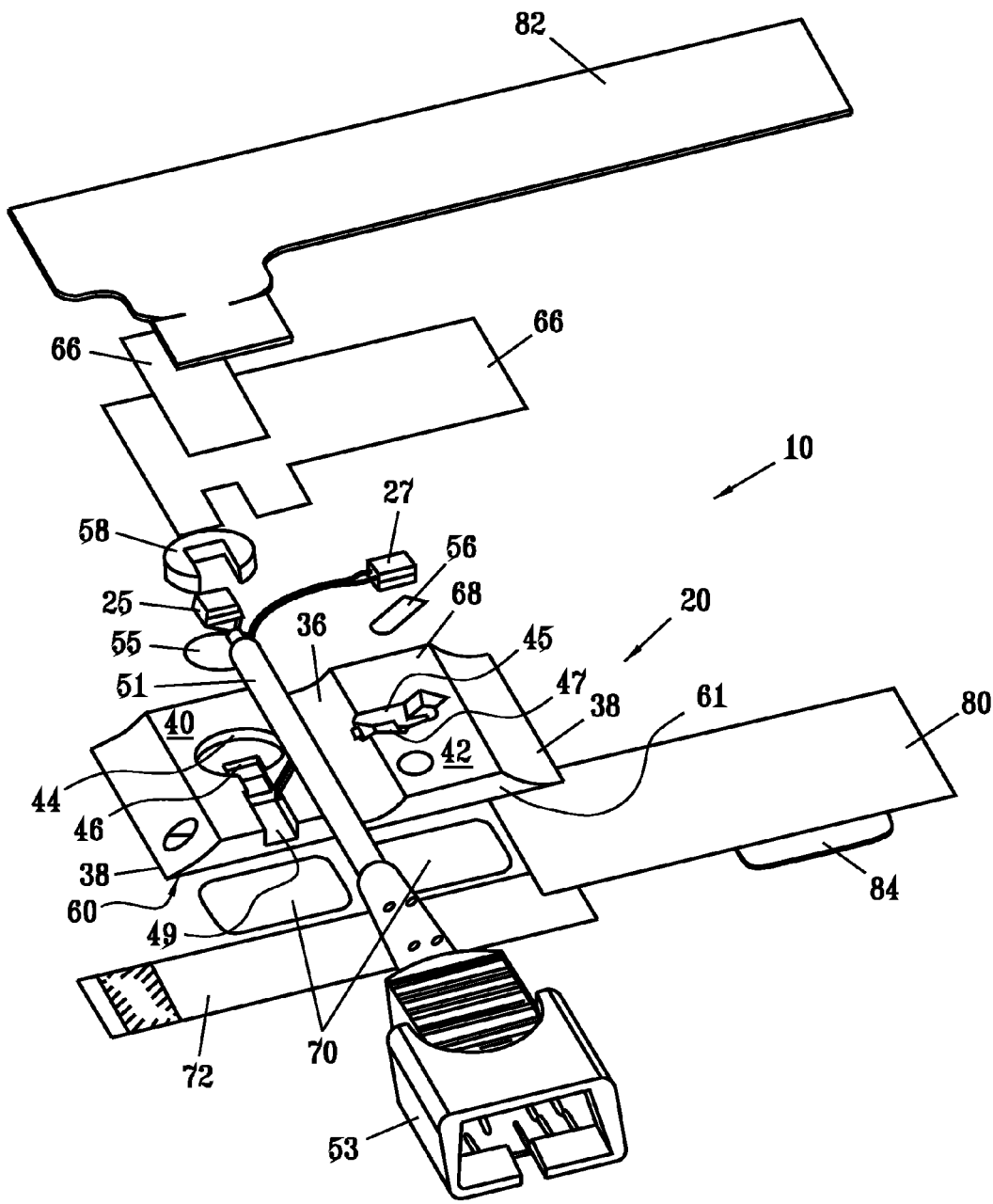
FIG. 4 illustrates an embodiment of a medical sensor of the present invention.

FIGS. 4-8 illustrate another embodiment of a medical sensor 10. As shown in FIG. 4, the medical sensor 10 includes a carrier band 20, detector 25, and emitter 27. The detector 25 and emitter 27 are mounted in recesses 44, 45, respectively. Connecting cable 51 is positioned in recess 49. The connecting cable 51 connects to the detector 25 and emitter 27 and provides a connection 53 to interface with the monitoring system containing necessary electronics components to provide power for the sensor and analyze the returned signals.

Figure 5:
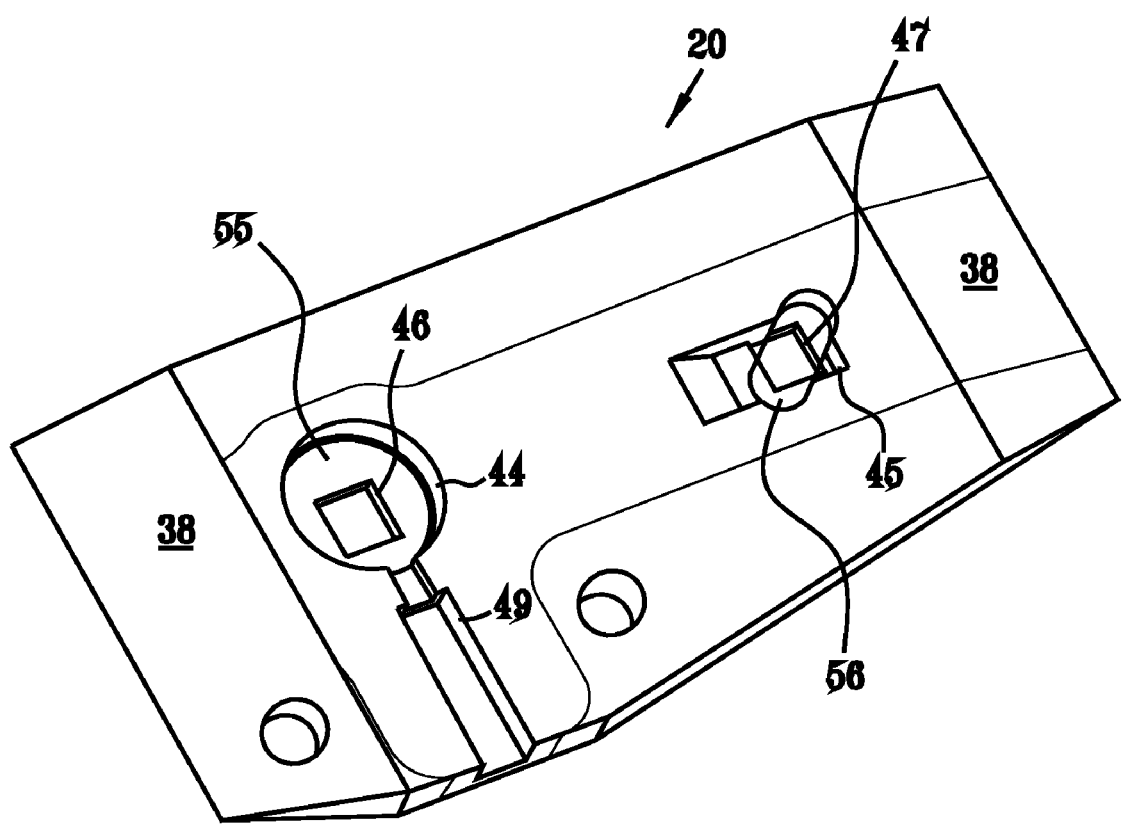
FIG. 5 illustrates an embodiment of a carrier band for a medical sensor.

As best shown in FIG. 5, inner windowpanes 55, 56 are inserted into recesses 46, 48, respectively, to cover the windows 46, 47. These inner windowpanes 55, 56 are generally a double-sided, clear adhesive that secures to the carrier band 20 and the detector 25 and emitter 27, while allowing light to pass there through to respective electrical components. A dark fitting piece 58 is secured around the detector 25 to assist in maintaining the location of the receiver and to prevent light shunting. In some embodiments, the fitting piece 58 is a black foam that is shaped to fit the detector 25. The detector 25 and fitting piece 58 are placed in recess 44 and secured by inner windowpane 55 on window 44. In this embodiment, the detector 25 is recessed approximately 1 mm from the top surface 60 of the carrier band 20. The emitter 27 is placed in recess 48 and secured by inner window 56. In this embodiment, the emitter 27 is also recessed approximately 1 mm from the top surface 60 of the carrier band 20. Connector cable 51 is run through recess 49 and out the end 61 of the carrier band 20.

Figure 6:
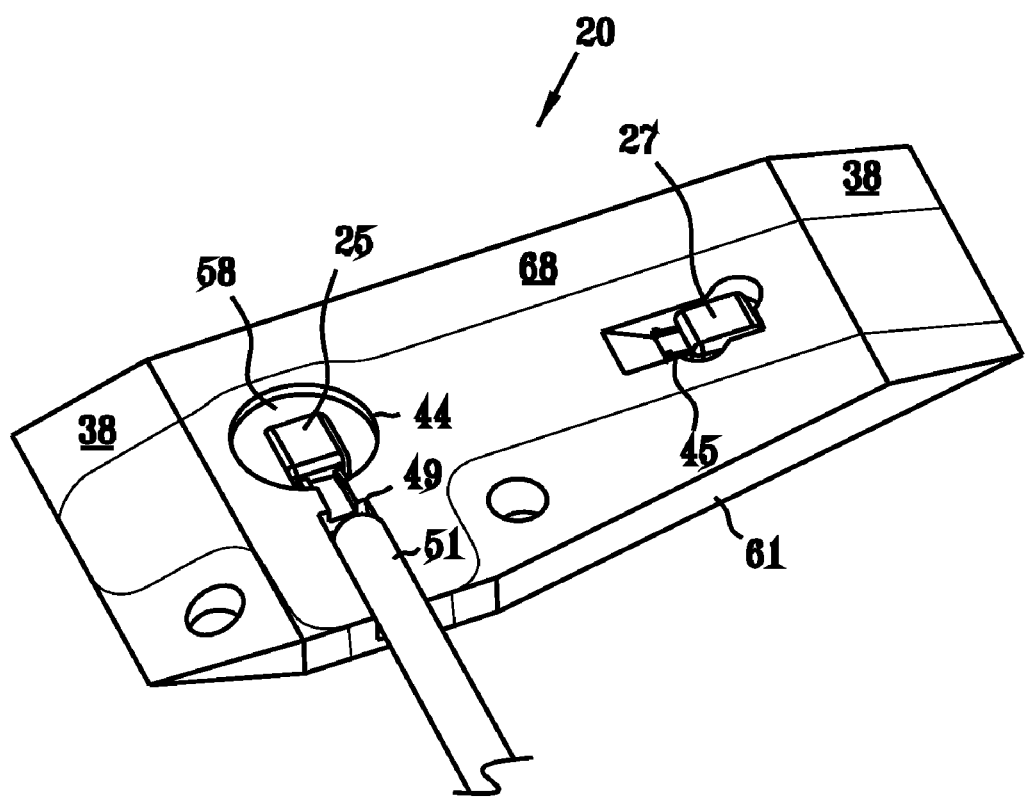
FIG. 6 illustrates the carrier band shown in FIG. 5 with a detector and an emitter secured in their respective recesses.
Figure 7:
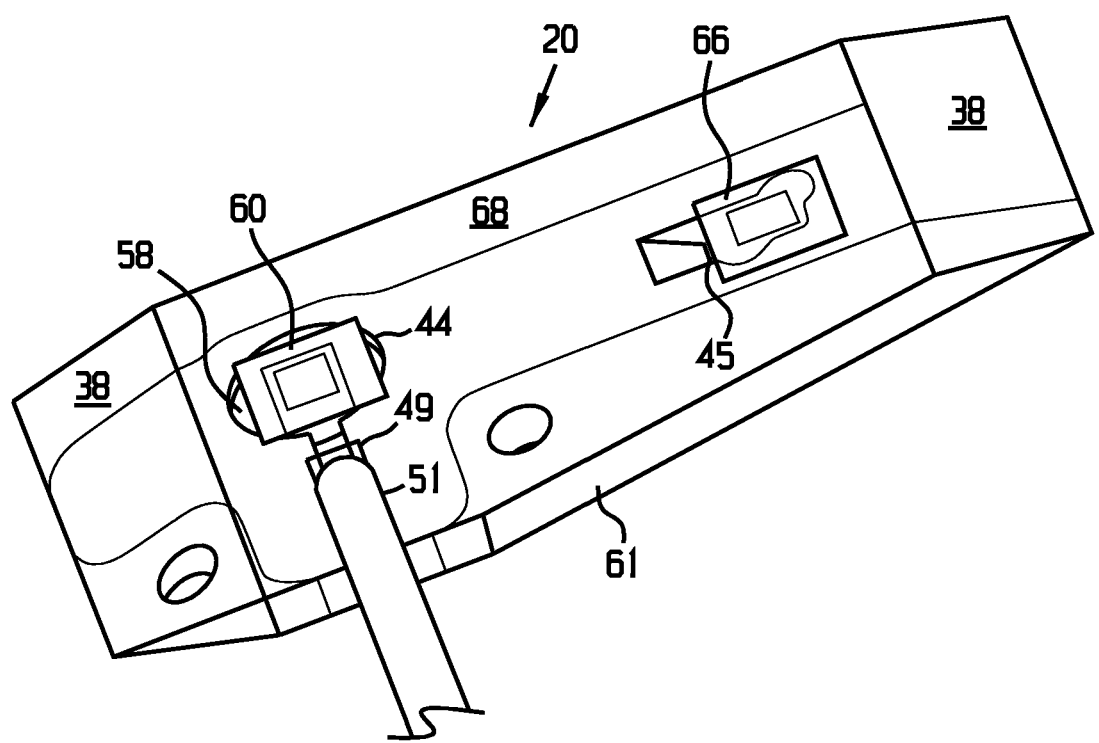
FIG. 7 illustrates the carrier band shown in FIG. 6 with light blockers covering the detector and emitter.
Figure 8:
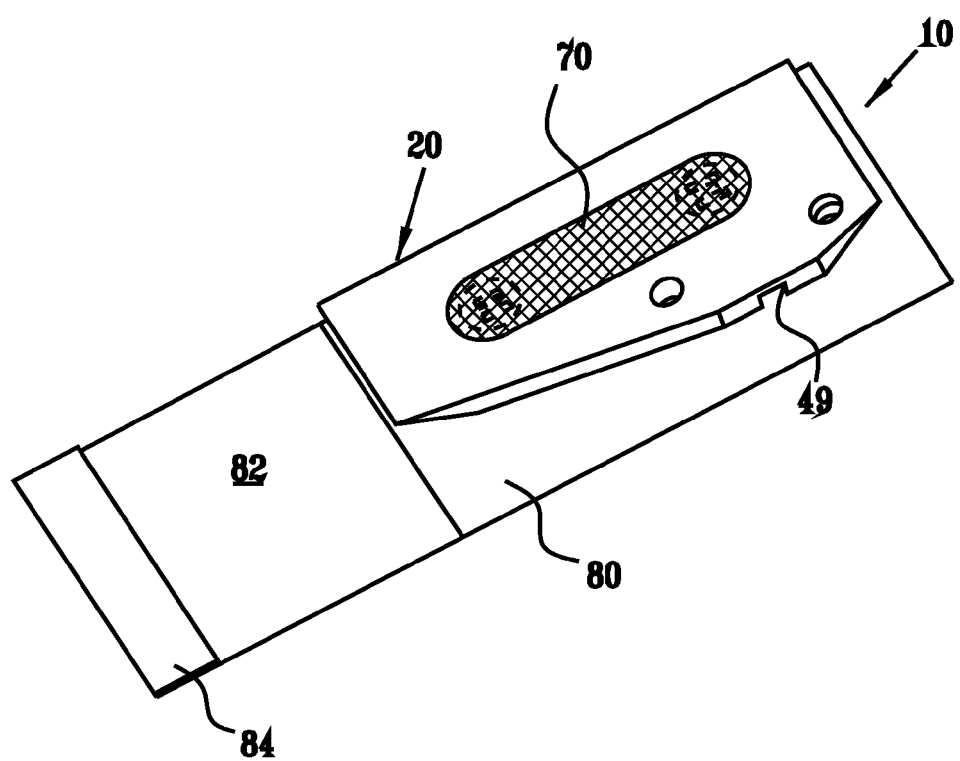
FIG. 8 illustrates the carrier band shown in FIGS. 5-8 attached to a hook and loop attachment means.

As shown in FIG. 6, one or more light blockers 66 are secured to the back surface 68 of the carrier band 20 such that the light blockers cover the detector 25 and emitter 27. The light blockers 66 prevent light from accessing the detector 25 and emitter 27 through the backside of the carrier band 20. The light blockers 66 can include one solid piece or several pieces and can be one or more layers. The light blockers 66 can be a reflective foil or other appropriate light blocking material.

On the top surface 60 of the carrier band 20, an adhesive liner or a set of adhesive pads 70 cover the windows 46, 47. The adhesive liner or pads 70 are clear, thereby allowing light to pass through to the electrical components 25, 27. A releasable material 72 is then used to cover the top surface 60 of the carrier band 20. The releasable material 72 covers the windows 46, 47 to prevent contamination while the medical sensor 10 is not in use. When the medical sensor 10 is to be applied to a patient, the material 72 is removed from the top surface 60 of the carrier band 20, thereby exposing the windows 46, 47 and hence the electrical components 25, 27.

An inner tape 80 is used to secure the carrier band 20 to a backing fabric loop material 82 and a strip of hook material 84. The backing fabric loop material 82 secures to the strip of hook material 84 to secure the medical sensor 10 in a wrapped position.

In order to apply the medical sensor 10 to a patient, the releasable material 70 is removed from the carrier band 20 and the applied part 30 is placed generally such that one sensing area of the applied part is generally centered on one of the windows 46. The medical senor 10 is then wrapped about the applied part 30, such that the other window 47 aligns substantially across from the positioned window 46, thereby aligning the detector 25 and the emitter 27. As the carrier band 20 wraps around the applied part 30, the thin groove portion 36 flexes and adapts to the contour of the applied part. The mounting areas 40, 42 act to spring the medical sensor into the wrapped position. The hook material 84 is then secured to the loop material 82, thereby securing the medical sensor 10 in the wrapped position around the applied part 30. The design of the carrier band 20 is such as to allow the medical sensor 10 to be applied to variably sized applied parts 30, while maintaining the alignment of the detector 25 and the emitter 27. The medical sensor 10 also provides an insulated space between the electrical components and the skin of the applied part. In addition, the design of the carrier band 20 is such as to facilitate easy and accurate application of the medical sensor.

The invention has been described with reference to one or more preferred embodiments. Clearly, modifications and alterations will occur to other upon a reading and understanding of this specification. For example, several improvements to medical sensors have been described herein. It is contemplated that each of these improvements can be applied separately, jointly, or in subcombinations to arrive at an improved medical sensor. It is intended to include all such modifications, combinations, and alterations insofar as they come within the scope of the appended claims or equivalents thereof.

The invention claimed is:

1. A medical sensor comprising:
    a foam carrier band including a thick detector mounting section and a thick emitter mounting section and a thin, flexible groove section disposed between and connecting the thick detector and emitter sections;
    a detector mounted in the thick detector mounting section of the carrier band; and
    an emitter mounted in the thick emitter mounting section of the carrier band,
    wherein the thin flexible groove section is configured to accommodate variably sized applied body parts, while maintaining substantial alignment of the detector directly opposite the emitter on an opposite side of the applied body part when applied to an applied part, wherein said carrier band includes an emitter window, the emitter window including a cut out region of the carrier band, a first layer of transparent material covering a first side of the cut out region, and a second layer of transparent material covering a second side of the cut out region, wherein an air gap defined between the first and second transparent material layers is provided between the emitter and the skin of the applied part.

2. The medical sensor of claim 1, wherein said carrier band is polyethylene.

3. The medical sensor of claim 1 further includes hook and loop material for securing the medical sensor in a wrapped position.

4. The medical sensor of claim 1 further comprising a detector window, wherein said detector window provides a space between the detector and the skin of the applied part.

5. The medical sensor of claim 1, wherein the medical sensor is a pulse oximetry sensor.

6. A medical sensor comprising:
    a carrier band which has a recessed portion in which a cut out portion is defined;
    a first clear layer disposed in the recessed portion covering one side of the cut out portion;
    a second clear layer disposed on an opposite side of the cut out portion such that an air gap is defined between the first and second clear layers;
    a detector mounted on a portion of the carrier band; and
    an emitter mounted in the recessed portion of the carrier band and disposed adjacent the first clear layer to emit light through the first and second clear layers and the air gap into a body part,
    wherein when the medical sensor is in a wrapped position around the body part, the air gap is disposed between the emitter and skin of the body part.

7. The medical sensor of claim 6, wherein the air gap between the emitter and the skin of the applied part is a predetermined distance.

8. The medical sensor of claim 6, wherein said carrier band is polyethylene foam.

9. The medical sensor of claim 6, wherein said carrier band comprises a thick detector mounting section, a thick emitter mounting section, and a thin flexible groove section disposed between and connecting the thick detector and emitter mounting sections.

10. The medical sensor of claim 6, wherein the medical sensor is a pulse oximetry sensor.

11. A medical sensor comprising:
    a carrier band including a thin section that facilitates wrapping of the carrier band and first and second thick sections that act as spring-loaded mounts when the carrier band is secured in a wrapped position around a body part, the thin section being disposed between and connecting the first and second thick sections;
    a detector mounted to a recessed region of the first thick section;
    a cut out region in the second thick section, a first layer of material on a first side of the carrier band covering the cut out region, and a second layer of material on a second side of the carrier band covering the cutout out region to define an air gap between the first and second material layers; and
    an emitter mounted adjacent the second material layer.

12. The medical sensor of claim 11, wherein said detector and said emitter are substantially aligned on opposite sides of the body part when said carrier band is in the wrapped position.

13. The medical sensor of claim 11, wherein said carrier band is polyethylene foam.

14. The medical sensor of claim 11, wherein the air gap keeps the emitter a predetermined distance from skin of the body part.

15. The medical sensor of claim 11, wherein the medical sensor is a pulse oximetry sensor.

* * * * *